United States Patent [19]

Schirmer

[11] Patent Number: 4,983,171
[45] Date of Patent: Jan. 8, 1991

[54] COMFORTABLE OSTOMY POUCH

[75] Inventor: Henry G. Schirmer, Spartanburg, S.C.

[73] Assignee: W. R. Grace & Co. - Conn., Duncan, S.C.

[21] Appl. No.: 379,856

[22] Filed: Jul. 14, 1989

[51] Int. Cl.$^5$ ............................................. A61M 1/00
[52] U.S. Cl. ........................................ 604/332; 604/337
[58] Field of Search ........................... 156/145, 306; 604/332-345; 206/438

[56] References Cited

U.S. PATENT DOCUMENTS

| 3,405,020 | 10/1968 | Chavannes | 156/306 |
| 3,416,984 | 12/1968 | Chavannes et al. | 156/209 |
| 3,586,565 | 6/1971 | Fielding | 156/210 |
| 3,785,899 | 1/1974 | Fielding | 156/209 |
| 4,314,865 | 2/1982 | Ottaviano | 156/145 |
| 4,412,879 | 11/1983 | Ottaviano | 156/145 |
| 4,415,398 | 11/1983 | Ottaviano | 156/470 |
| 4,427,474 | 1/1984 | Ottaviano | 156/145 |
| 4,439,191 | 3/1984 | Hogan | 604/332 |
| 4,576,669 | 3/1986 | Caputo | 156/145 |
| 4,579,516 | 4/1986 | Caputo | 425/388 |
| 4,687,711 | 8/1987 | Vietto et al. | 428/515 |
| 4,724,185 | 2/1988 | Shah | 428/339 |
| 4,826,493 | 5/1989 | Martini et al. | 604/327 |

FOREIGN PATENT DOCUMENTS 2415943  8/1979  France ................................ 206/522

Primary Examiner—Randall L. Green
Assistant Examiner—Gary Jackson
Attorney, Agent, or Firm—John J. Toney; Mark B. Quatt; Jennifer L. Skord

[57] ABSTRACT

Disclosed is an ostomy bag that is made with air cushion film so that the air bubbles are on the bag outside. Air cushion film is known as bubblepak in the industry. The bubbles afford a high degree of comfort to the person wearing the ostomy bag.

6 Claims, 3 Drawing Sheets

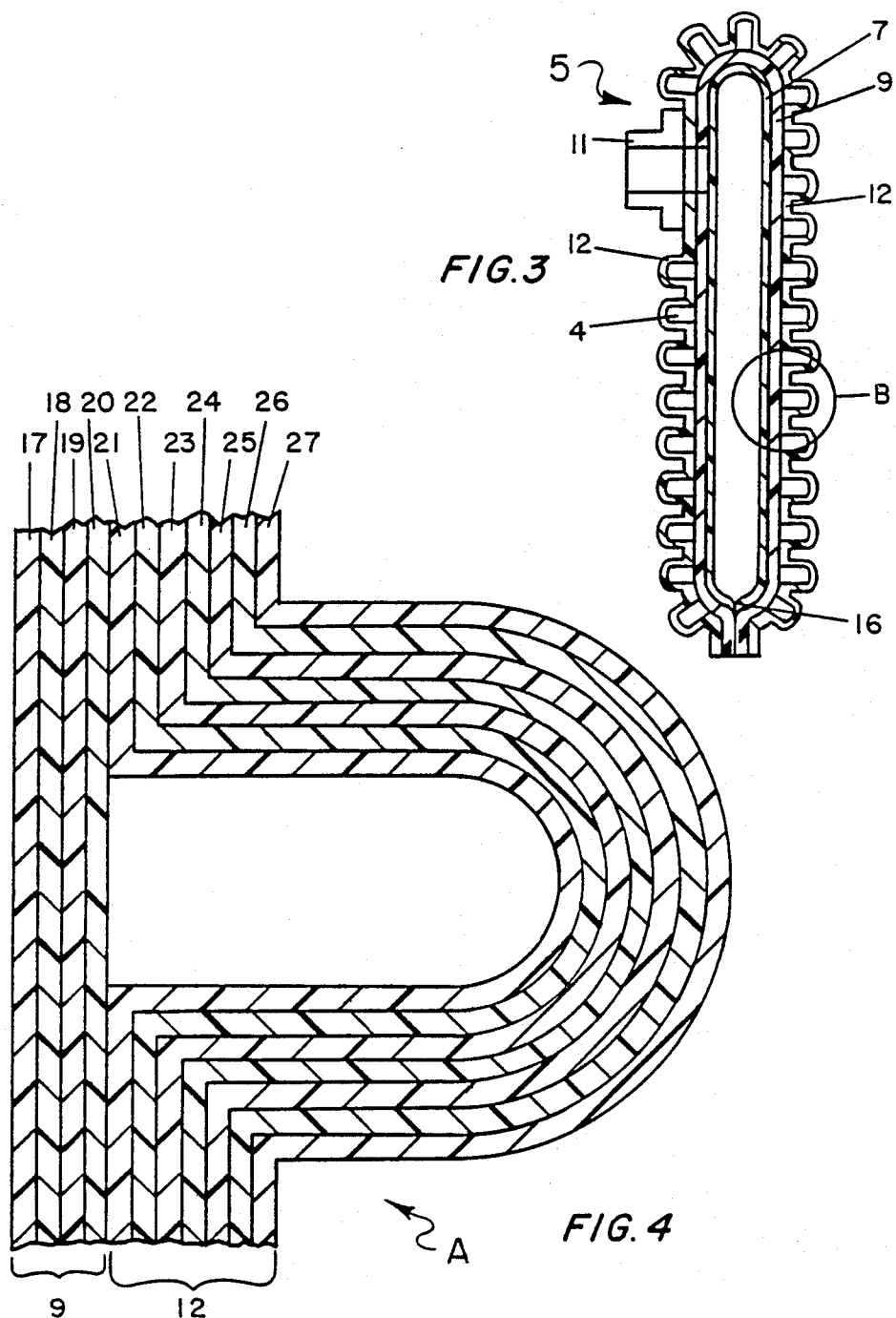

COMFORTABLE OSTOMY POUCH

BACKGROUND OF THE INVENTION

This invention relates to the technical field of laminated films and related articles of manufacture, such as bags and containers, particularly for ostomy.

More specifically, the invention concerns flexible polymeric air cushion films (air cushion film is colloquially referred to as "bubble cap" or "bubblepak"), which lend themselves specially well to the manufacture of containers and bags intended for human drainage in medical applications, and particularly for collecting excretion products from patients whose excretive apparatus has been reconstructed surgically.

Easily pictured, and readily ascertainable, is the discomfort suffered by patients who, after undergoing surgical intervention to reconstruct or deviate their excretive apparatus following traumatic or pathological events in particular of the tumoral type, then must carry along a personal plastic container of excretion products continuously during their active life.

In general, such patients find themselves with an artificial anus formed from a protruding intestinal portion connected to a collecting plastic container which is carried at the waist region against the skin, under the patient's garments.

There exist a few features that a patient of the kind in question would welcome of such a container, the presence of which container should desirably pass unnoticed by other persons met in the course of the patient's activities.

Currently available from a number of manufacturers are excretion product collection containers which meet some of the requirements set forth by deviated excretion apparatus patients; these containers, which are formed generally from plastic film materials, exhibit features which could be regarded as reasonably satisfactory for the using patient; among these, mechanical properties may be mentioned which afford a good degree of protection against wear, abrasion, and puncturing, as well as gas and odor barrier properties. Prior ostomy bags are disclosed in U.S. Pat. No. 4,687,711 and U.S. Pat. No. 4,826,493.

However, and beyond the results achieved thus far, there still exists the need for comfort.

The containers employed in the past exhibit a texture and "feel" which make them less than ideally suited to applications involving compatibility with human skin, whereby the patient is never allowed at least occasionally "to forget" his/her disabled condition, with obvious disturbing consequences of a psychological nature. The plastic is lying up against the skin. The skin sweats. The plastic sticks and rubs. The result goes from annoying, to irritation, to rash, particularly during hot humid summer months.

OBJECTS OF THE INVENTION

It is an object of this invention, in order to correct such prior deficiencies, to provide a film which, additionally to desirable properties of resistance to wear, abrasion, and puncturing, and properties as a gas and odor barrier, has improved comfort features characterized by an air cushion, such that the bubbles of the air cushion minimize film contact with the skin and prevent moisture build-up with free ventilation.

Another object of the invention, consequent to the former, is to provide bags or containers intended in particular for human draining and collecting excretion products from patients having a deviated reconstructed excretive apparatus, which exhibit high comfort and human skin compatibility features.

It has been unexpectedly found that the foregoing objects, and others which will be apparent hereinafter, can be achieved according to the present invention by a film formed from air cushion, said air cushion imparting the film with high comfort characteristics.

According to a further aspect of the invention, there are provided drainage containers or bags for medical applications, useful to collect excretion products from patients whose excretive apparatus has been reconstructed and/or deviated, characterized by comfort properties as well as by properties of resistance to wear, abrasion, and puncturing, and of gas and odor barrier, said bags or containers being formed from a laminated film comprised of said air cushion.

SUMMARY OF THE INVENTION

Therefore, the present invention provides an ostomy pouch having a high degree of comfort comprising a multi-ply air cushion laminate containing (a) a forming web ply of air cushion bubbles including a barrier layer, said air cushion bubbles defining the bag outside, (b) a non-forming web ply including a barrier layer, said non-forming web laminated on one surface thereof to the forming web, and (c) an ostomy fitting sealed to the laminate for attachment to a patient.

This invention also provides method of improving the comfort of an ostomy bag, comprising forming a bag by providing an air cushion film containing a non-forming web ply laminated on one surface thereof to a forming web ply of air cushion bubbles, said non-forming web ply and said forming web ply each including a barrier layer, the other surface of the non-forming web ply optionally being laminated to another ply, sealing the facing portions of the bag inside around their periphery so that the forming web ply of air cushion bubbles defines the bag outside to be in contact with human skin, and sealing the bag to a fitting for attachment to a patient tube.

The invention also provides an ostomy bag having a high degree of comfort comprising a multi-ply air cushion laminate containing (a) a forming web ply of air cushion bubbles, said bubbles defining the bag outside, and wherein said forming web ply is of the multi-layer structure linear low density polyethylene/ethylene-vinyl acetate/adhesive/nylon/ adhesive/ethylenevinyl acetate/ethylene vinyl acetate, (b) a non-forming web ply of the multi-layer structure: ethylene-vinyl acetate/polyvinylidene chloride/ethylene-vinyl acetate/linear low density polyethylene, laminated on its ethylene-vinyl acetate surface layer to the ethylene-vinyl acetate surface layer of the forming web ply, wherein facing portions of the bag inside are sealed around their periphery, and (c) an ostomy fitting sealed to the laminate for attachment to a patient.

DETAILED DESCRIPTION OF THE INVENTION AND OF THE DRAWINGS

Ostomy bags are generally made from a laminate containing at least a barrier layer of polyvinylidene chloride (to give impermeability) with a surface layer of ethylene vinyl acetate (to give softness and heat sealability).

Many non-barrier polymer resins are suitable for one or more layers of an ostomy bag. These include, but are not limited to, materials such as polyethylene (PE), polypropylene (PP), ethylene-vinyl acetate (EVA), linear low density polyethylene (LLDPE), high density polyethylene (HDPE), medium density polyethylene (MDPE), low density polyethylene (LDPE), very low density linear polyethylene (VLDPE), ethylene/alkylacrylate copolymer (EAlAcr), ethylene/propylene copolymer (EPC), and the like, the homopolymers, copolymers, terpolymers, etc thereof, and blends and modifications thereof. Also suitable is hydroxy butyric acid polymer (HB), which is biodegradable; this is disclosed in U.S. Pat. No. 4,826,493, the disclosure of which is incorporated herein by reference.

Blends of EVA, EPC, HB, EAlAcr, PP, LDPE, HDPE, VLDPE, and LLDPE may also be advantageously employed.

Ostomy bags also contain a barrier layer and the air cushion ostomy film of the invention contains a barrier layer. The layer is a barrier to odors and to fluids such as water and gas. The barrier layer may be composed of a layer comprising vinylidene chloride copolymer, typically with a comonomer selected from acrylic ester, acrylic acid, and vinyl chloride (commonly known as saran), or composed of a layer comprising hydrolyzed ethylene-vinyl acetate copolymer (EVOH), preferably hydrolyzed to at least about 50%, most preferably to greater than about 99%, or composed of a layer comprising polyamide (commonly known as nylon). An excellent barrier could be the multilayer coextruded film in U.S. Pat. No. 4,724,185 to Shah, the disclosure of which is incorporated herein by reference. This multilayer film has a core barrier ply that is a blend of polyamide and EVOH. The oxygen transmission rate of the barrier layer should be below 150, more preferably below 70 cc/sq. m/ mil thickness/24 hours/atm as measured by ASTM D-3985.

As mentioned above, the air cushion film contains a forming web and a non-forming web.

A suitable multilayer film useful for the ply for the forming web is of the 7-layer structure: LLDPE/EVA/adhesive/nylon/adhesive/EVA or LLDPE/EVA. The last EVA layer is the sealing layer that is laminated to the non-forming web. The EVA should be high in % VA for softness, typically 18 to 28% VA. Suitable EVA resin is sold by duPont under the trademark Elvax 3182 or Elvax 3130. The LLDPE should be thin for softness; it is desired to use LLDPE to provide a heat barrier during the thermal lamination to seal the forming web and non-forming web together when making air cushion as the LLDPE side is what touches the hot forming roller of the air cushion machine. Suitable LLDPE resin is sold by Dow Chemical under the trademark Dowlex 2035. Suitable adhesive resins are sold by duPont under the trademark Bynel or sold by Quantum/USI under the trademark Plexar. A suitable nylon is nylon 6 sold under the trademark Grilon CF6S by Emser.

A suitable multilayer film useful for the ply for the non-forming web is of the structure: EVA/SARAN/EVA, optionally EVA/SARAN/EVA/LLDPE, where the first EVA layer is the sealing layer that is laminated to the forming web. Commercially available EVA and LLDPE as mentioned in the paragraph above may be employed. Suitable saran resin is polyvinylidene chloridemethyl acrylate sold by Dow Chemical under the trade name XU32034.00.

The starting film used for preparing the air cushion films of this invention may be prepared with conventional methods, effecting, for example, a compounding step in accordance with conventional industrial practice, e.g. by means of an extruder.

Where it is desirable to control further the surface properties, the polymer may have added a master batch of the type commonly employed in processing polymers.

The film is fashioned to have cushioning characteristics by using bubble cap (also known as air cushioning) machinery, such as that described in U.S. Pat. Nos. 4,576,669 and 4,579,516, both to Caputo, or that described in U.S. Pat. Nos. 4,314,865 (Feb. 9, 1982), 4,415,398 (Nov. 15, 1983; divisional of 4,314,865), 4,427,474 (Jan. 24, 1984; Terminal Disclaimer Requiring Expiration on Same Date as 4,314,865), and 4,412,879 (Nov. 1, 1983), all by inventor Ottaviano, or that described in U.S. Pat. Nos. 3,416,984, 3,405,020, 3,586,565, and 3,785,899, all assigned to Sealed Air, the disclosures of which are incorporated herein by reference, to make a bubble cap laminate which provides cushioning and then the laminate is made into a bag or pouch by conventional methods.

As discussed above, the air cushion film will have laminated together a bubble or blister ply (which may have one or more polymeric layers) called the forming web (below referred to as A) and another ply (which may have one or more polymeric layers) called the non-forming web (below referred to as B). When the air cushion film is made into a bag, the non-forming web will be facing inside the bag, and the forming web will be facing outside the ostomy bag. The bubbles or blisters thus face outwards and contact the body but the areas around the bubbles do not, thus affording minimum contact with the skin to alleviate sweating and promote ventilation. Optionally, the other surface of the non-forming web may be laminated to another ply such as a layer of another odor barrier film (below referred to as optional C) defining the bag inside.

A simple example of a multilayer laminated film having such characteristics comprises multilayer laminated film of the A/B/C type, where A is a ply of the forming web of bubbles, B is the non-forming web, and C is optionally another odor barrier ply. In this case, the overall thickness of the multi-ply laminated film may be, for example, on the order of 65 to 110 microns, while the thicknesses of the ply A and ply B may be preferably and approximately in the 12.5 to 32.5 microns range for the layer A, and approximately in the 40 to 80 microns range for the barrier ply B.

Of course, the thicknesses of the plies A and B, and the arrangement and number of the plies may vary somewhat to meet individual requirements.

The bubbles are typically ¼ inch to ⅜ inch in diameter and ⅛ inch to ⅜ inch high. But smaller or larger may be desirable in some instances.

Such a multilayer film, and particularly the multi-ply film of the A/B type or the A/B/C type described hereinabove, lends itself quite well to the manufacture of containers and bags. Such containers and bags are soft and pliable, are comfortable, are resistant to thermal and mechanical stresses, and the heat-welded film edges invariably meet the safety requirements imposed on them.

Such bags and containers, when placed in contact with skin, alleviate unpleasant feelings; the patient experiences no inconvenience or embarrassment as the minimization of skin contact alleviates the moisture problem from plastic causing skin to sweat.

FIG. 3 is a cross-section showing a variation with another ply inside the bag.

FIG. 4 is a blow-up of circle A in FIG. 2 showing the layers of each ply.

Figure 1:
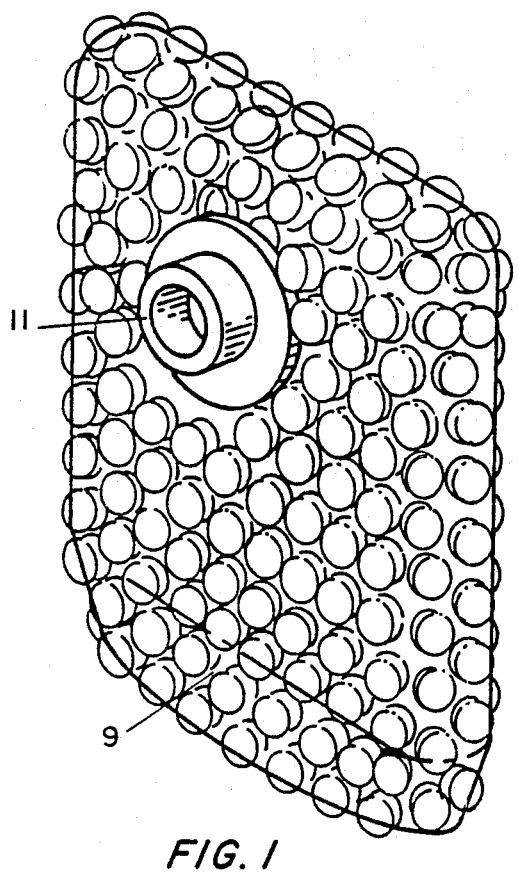
FIG. 1 is a perspective view of an ostomy bag 3.
Figure 2:
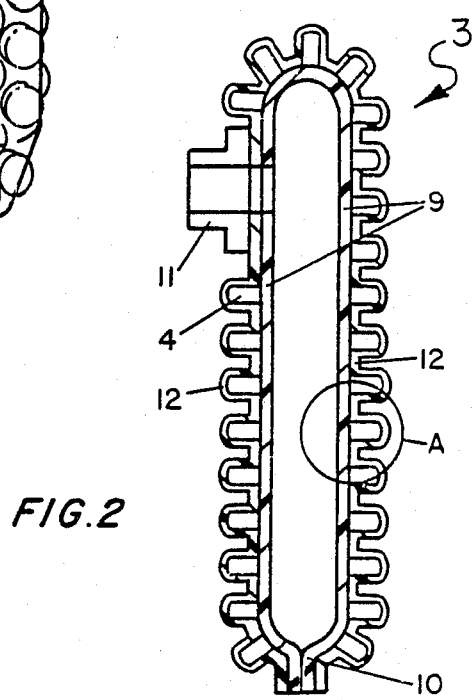
FIG. 2 is a cross-section through the bag of FIG. 1.

The ostomy bag in FIGS. 1 and 2 comprises an air cushion film formed into a pouch 3 and melt sealed around its inside facing edges 10, and melt sealed to an ostomy fitting 11. Ply 12 comprises the forming web of bubbles and is laminated to ply 9, the non-forming web. Aperature 4 is illustrative of the trapped air bubble that is caught between the bubble ply 12 and ply 9 when these two plies are laminated together. Ply 9 defines the bag inside. Bubble ply 12 faces outwards and is that which will touch the skin when the bag is used. Each of ply 12 and ply 9 contains a barrier layer, not illustrated.

FIG. 3 shows in cross-section an optional embodiment of an ostomy bag 5 wherein the air cushion film is laminated on its non-forming web side 9 to another ply 7 such as an odor barrier layer. In that instance, the pouch is melt sealed around its inside facing edges 16, as ply 7 defines the bag inside.

FIG. 4 is a blow up of circle A of FIG. 2 showing the layers of each ply of the preferred embodiment. Illustrated are layer 17 of LLDPE, layer 18 of EVA, layer 19 of PVDC, and layer 20 of EVA, the four layers forming ply 9. Also illustrated is layer 21 of EVA, layer 22 of EVA, layer 23 of adhesive, layer 24 of nylon 6, layer 25 of adhesive, layer 26 of EVA, and layer 27 of LLDPE, the seven layers being of bubble ply 12.

Figure 5:
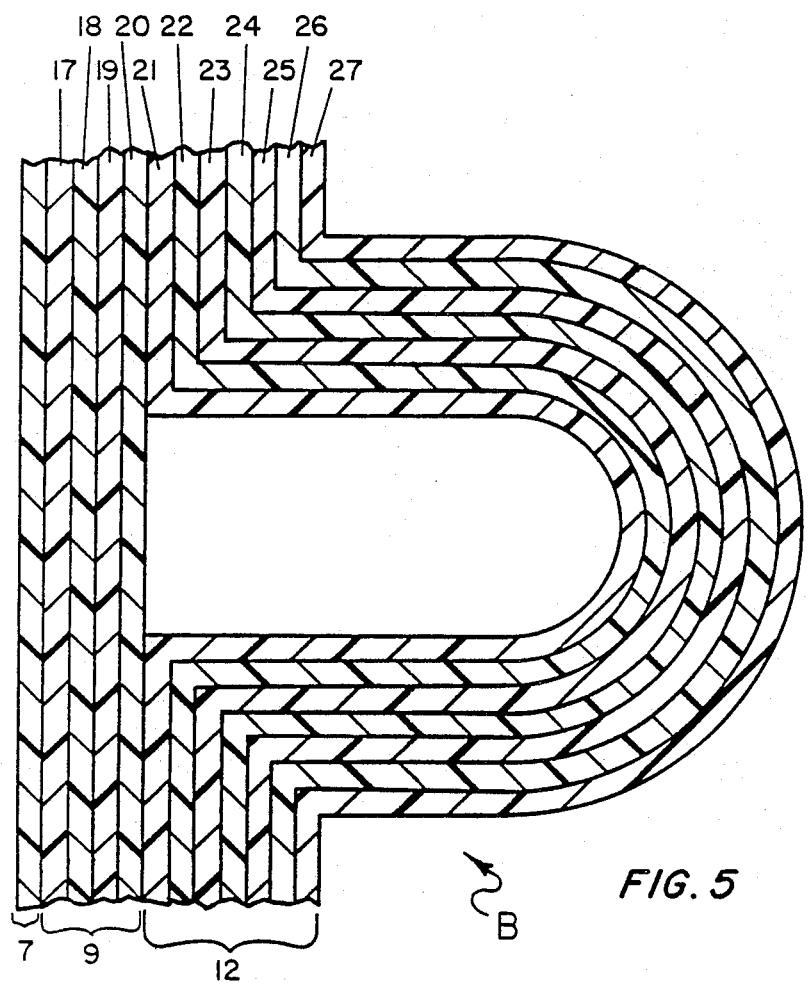
FIG. 5 is a blow-up of circle B in FIG. 3 showing the layers of each ply.

FIG. 5 is a blow up of circle B of FIG. 3 showing the layers of each ply of another preferred embodiment. Illustrated are layer 17 of LLDPE, layer 18 of EVA, layer 19 of PVDC, and layer 20 of EVA, the four layers being of ply 9. Also illustrated is layer 21 of EVA, layer 22 of EVA, layer 23 of adhesive, layer 24 of nylon 6, layer 25 of adhesive, layer 26 of EVA, and layer 27 of LLDPE, the seven layers being of bubble ply 12. Lastly, illustrated is optional ply 7 laminated to the LLDPE surface, namely layer 17 of ply 9.

The example which follows only purports to illustrate the invention and not to restrict its field of application and serves the purpose of emphasizing the degree of effectiveness achieved thereby.

EXAMPLE

A forming web and a non-forming web are fed into an air cushion machine and air cushion laminate is made. The forming web from outside layer to sealing layer is of the structure: LLDPE/EVA/adhesive/nylon 6/adhesive/EVA/EVA. It is 1 mil (25 microns) thick. The non-forming web from sealing layer to outside layer is of the structure: EVA/SARAN/EVA/LLDPE. It is 3 mils (76 microns) thick. Thus, when the 2 webs are joined in the air cushion laminate, it is their respective EVA surfaces that are sealed together. The bubbles are about ⅛ inch high and ⅛ inch in diameter. The air cushion is folded over with the bubbles on the outside and the facing portions of the bag inside are sealed around their periphery to form an ostomy pouch. Also the pouch is sealed to an ostomy fitting for attachment to the tube that comes out of the patient. The LLDPE layer of the non-forming web is the bag inside.

I claim:

1. An ostomy pouch having a high degree of comfort comprising a polymeric plastic multi-ply air cushion laminate containing:
   (a) a polymeric plastic forming web ply of air cushion bubbles including a barrier layer, said air cushion bubbles defining the bag outside,
   (b) a polymeric plastic non-forming web ply including a barrier layer, said non-forming web laminated on one surface thereof to the forming web, and
   (c) an ostomy fitting sealed to the laminate for attachment to a patient,
   (d) such that the air cushion bubbles minimize contact with the patient's skin and prevent moisture build-up and provide free ventilation.

2. The ostomy pouch of claim 1, wherein the bubbles are ⅛ to ¼ inch high and ⅛ to ¼ inch in diameter.

3. The ostomy pouch of claim 1, having an oxygen transmission rate below 150 cc/square meter/mil thickness/24 hours/atmosphere.

4. The ostomy pouch of claim 1, wherein the forming web ply contains a layer of nylon and the non-forming web ply contains a layer of polyvinylidene chloride.

5. The ostomy pouch of claim 1, wherein the forming web ply is 12.5 to 32.5 microns thick and the non-forming web ply is 40 to 80 microns thick.

6. An ostomy bag having a high degree of comfort comprising a polymeric plastic multi-ply air cushion laminate containing:
   (a) a polymeric plastic forming web ply of air cushion bubbles including a barrier layer, said bubbles defining the bag outside, and wherein said forming web ply is of the multi-layer structure linear low density polyethylene/ethylene-vinyl acetate/adhesive/nylon/adhesive/ethylene-vinyl acetate-/ethylene vinyl acetate,
   (b) a polymeric plastic non-forming web ply of the multi-layer structure: ethylene-vinyl acetate/-polyvinylidene chloride/ethylene-vinyl acetate/-linear low density polyethylene, laminated on its ethylene-vinyl acetate surface layer to the ethylene-vinyl acetate surface layer of the forming web ply, wherein facing portions of the bag inside are sealed around their periphery, and
   (c) an ostomy fitting sealed to the laminate for attachment to a patient,
   (d) such that the air cushion bubbles minimize contact with the patient's skin and prevent moisture build-up and provide free ventilation.

* * * * *